United States Patent

Ross et al.

[11] Patent Number: 5,635,494
[45] Date of Patent: Jun. 3, 1997

[54] DIHYDROPYRIDAZINONES AND PYRIDAZINONES AND THEIR USE AS FUNGICIDES AND INSECTICIDES

[75] Inventors: Ronald Ross, Jamison; Steven H. Shaber, Horsham; Edward M. Szapacs, Center Valley, all of Pa.

[73] Assignee: Rohm and Haas Company, Philadelphia, Pa.

[21] Appl. No.: 426,514

[22] Filed: Apr. 21, 1995

[51] Int. Cl.$^6$ .......... A01N 55/10; A01N 43/58; C07D 237/14; C07D 237/16
[52] U.S. Cl. .......... 514/63; 514/85; 514/236.5; 514/247; 514/252; 514/253; 514/254; 544/114; 544/229; 544/232; 544/238; 544/239; 544/240; 544/241
[58] Field of Search .......... 544/114, 229, 544/232, 238, 239, 240, 241; 514/63, 85, 236.5, 247, 252–254

[56] References Cited

U.S. PATENT DOCUMENTS

| | | | |
|---|---|---|---|
| 4,914,128 | 4/1990 | Schirmer et al. | 514/532 |
| 4,937,372 | 6/1990 | Wenderoth et al. | 560/55 |
| 4,999,042 | 3/1991 | Anthony et al. | 504/235 |
| 5,041,618 | 8/1991 | Brand et al. | 560/104 |
| 5,055,471 | 10/1991 | de Fraine et al. | 544/239 |
| 5,157,144 | 10/1992 | Anthony et al. | 560/35 |
| 5,185,342 | 2/1993 | Hayase et al. | 514/274 |
| 5,194,662 | 3/1993 | Brand et al. | 560/35 |
| 5,221,691 | 6/1993 | Clough et al. | 514/619 |
| 5,315,025 | 5/1994 | Bushell et al. | 560/60 |
| 5,434,267 | 7/1995 | Kravs et al. | 544/239 |

FOREIGN PATENT DOCUMENTS 4305502  8/1994  Germany.

*Primary Examiner*—Emily Bernhardt
*Attorney, Agent, or Firm*—Joseph F. Leightner

[57] ABSTRACT

Compounds with fungicidal and insecticidal properties having formula I

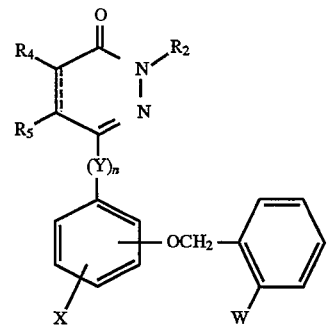

wherein
W is $CH_3-O-A=C-CO(V)CH_3$; n is 0 or 1;
A is N or CH;
V is O or NH;
wherein
Y is O, S, $NR_1$, or $R_6$, the ring bond containing $R_4$ and $R_5$ is a single or double bond and $R_4$ and $R_5$ are independently selected from hydrogen and substituted or unsubstituted alkyl and aryl groups.

20 Claims, No Drawings

DIHYDROPYRIDAZINONES AND PYRIDAZINONES AND THEIR USE AS FUNGICIDES AND INSECTICIDES

This invention relates to dihydropyridazinones, pyridazinones and related compounds, compositions containing these compounds and methods for controlling fungi and insects by the use of a fungitoxic and insecticidal amount of these compounds.

Patent application Ser. No. 91-308,404.2 published Sep. 13, 1991, entitled "Dihydropyridazinones, Pyridazinones and Related Compounds and Their Use As Fungicides" discloses pyridazinone compounds as effective fungicides. These pyridazinones fail to posses a phenyl substituted ring substituted with a β-methoxy methyl acrylates, a methoxyiminoacetate or a methoxyiminoacetamide. The present inventions are novel compositions which have also been discovered to possess fungicidal and insecticidal properties.

The dihydropyridazinones and pyridazinones of the present invention have the Formula (I)

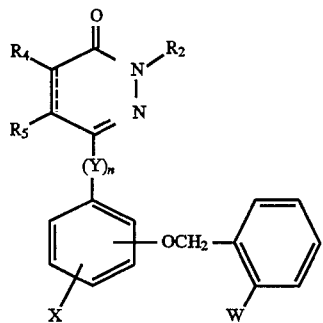

wherein

W is $CH_3$—O-A=C—CO(V)$CH_3$; A is N or CH; V is O or NH; n is 0 or 1;

Y is O, S, $NR_1$, or $R_6$, the ring bond containing $R_4$ and $R_5$ is a single or double bond;

X is independently selected from hydrogen, halo, $(C_1-C_4)$ alkyl, $(C_1-C_4)$alkoxy and —HC=CH—CH=CH— thereby forming a napthyl ring;

$R_2$ is independently selected from hydrogen, $(C_1-C_{12})$ alkyl, $(C_1-C_{12})$alkoxy, halo$(C_1-C_{12})$alkyl, halo $(C_1-C_{12})$alkoxy, hydroxy$(C_1-C_{12})$alkyl, $(C_1-C_{12})$ alkoxy$(C_1-C_{12})$alkyl, $(C_1-C_{12})$alkoxycarbonyl $(C_1-C_{12})$alkyl, $(C_2-C_8)$alkenyl, halo$(C_2-C_8)$alkenyl, $(C_3-C_{10})$alkynyl, halo$(C_3-C_{10})$alkynyl, $(C_3-C_7)$ cycloalkyl, $(C_3-C_7)$cycloalkyl$(C_1-C_4)$alkyl, epoxy $(C_1-C_{12})$alkyl, $PO(OR_1)_2(C_1-C_{12})$alkyl, $R_1S(O)_2$ $(C_1-C_{12})$alkyl, $(R_1)_3Si(C_1-C_{12})$alkyl, aryl, aryloxy $(C_1-C_{12})$alkyl, arylcarbonyl$(C_1-C_{12})$alkyl, aralkyl, arylalkenyl, heterocyclic, heterocyclic $(C_1-C_{12})$alkyl, N-morpholino$(C_1-C_{12})$alkyl, N-piperidinyl$(C_1-C_{12})$ alkyl;

$R_1$ is independently selected from $(C_1-C_{12})$alkyl, $(C_2-C_8)$ alkenyl and aryl;

$R_4$, and $R_5$ are independently selected from hydrogen, halo, $(C_1-C_8)$alkyl, $(C_1-C_8)$alkoxy, cyano, halo $(C_1-C_{12})$alkyl, $(C_2-C_8)$alkenyl, $(C_3-C_{10})$alkynyl, aryl and aralkyl; and $R_6$ is $(C_1-C_{12})$alkylenyl and $(C_2-C_{12})$ alkenylenyl.

The aforementioned $(C_1-C_{12})$alkyl, $(C_1-C_{12})$alkoxy, $(C_2-C_8)$alkenyl, $(C_3-C_{10})$alkynyl and $(C_3-C_7)$cycloalkyl groups may be optionally substituted with up to three substituents selected from the group consisting of halogen, nitro, trihalomethyl and cyano.

The term alkyl includes both branched and straight chained alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and 1 or 2 acetylenic bonds.

The term alkylenyl refers to a bivalent alkyl group in which two free bonds can be on the same carbon or different carbons. The term alkenylenyl refers to a bivalent alkenyl group in which the two free bonds are on different carbons, an alkenyl group may also be substituted with 1 to 3 halo atoms.

The term cycloalkyl refers to a saturated ring system having 3 to 7 carbon atoms.

The term aryl includes phenyl or napthyl, which maybe substituted with up to three substituents selected from the group consisting of halogen, cyano, nitro, trihalomethyl, phenyl, phenoxy, $(C_1-C_4)$alkyl, $(C_1-C_4)$alkylthio, $(C_1-C_4)$ alkylsulfoxide $(C_1-C_6)$alkoxy and halo$(C_1-C_4)$alkyl.

Typical aryl substituents include but are not limited to 4-chlorophenyl, 4-fluorophenyl, 4-bromophenyl, 2-methoxyphenyl, 2-methylphenyl, 3-methyphenyl, 4-methylphenyl, 2,4-dibromophenyl, 3,5-difluorophenyl, 2,4,6-trichlorophenyl, 4-methoxyphenyl, 2-chloronapthyl, 2,4-dimethoxphenyl, 4-(trifluoromethyl)phenyl and 2-iodo-4-methylphenyl.

The term heterocyclic refers to a optionally substituted 5 or 6 membered unsaturated ring containing one, two or three heteroatoms, preferably one or two heteroatoms selected from oxygen, nitrogen and sulfur or is a bicyclic unsaturated ring system containing up to 10 atoms including one heteratom selected from oxygen, nitrogen and sulfur. Examples of heterocycles includes but is not limited to 2-, 3- or 4-pyridinyl, pyrazinyl, 2-, 4-, or 5-pyrimidinyl, pyridazinyl, triazolyl, imidazolyl, 2 - or 3-thienyl, 2- or 3-furyl, pyrrolyl, oxazolyl, isoxazolyl, thiazolyl, isothiazolyl, oxadiazolyl, thiadiazolyl, quinolyl andisoquinolyl. The heterocyclic ring may be optionally substituted with upto two substituents independently selected from $(C_1-C_2)$ alkyl, halogen, cyano, nitro and trihalomethyl.

The term aralkyl is used to describe a group wherein the the alkyl chain is from 1 to 10 carbon atoms and can be branched or straight chain, preferably a straight chain, with the aryl portion as defined above. Typical aralkyl substituents include but are not limited to 2-chlorobenzyl, 3-chlorobenzyl, 4-chlorobenzyl, 4-fluorobenzyl, 4-trifluoromethylbenzyl, 2,4-dichlorobenzyl, 2,4-dibromobenzyl, 4-chlorophenethyl, 4-fluorophenethyl, 4-trifluoromethylphenethyl, 3-methylphenethyl, 4-methylphenethyl, 2,4-dichlorophenethyl, 3,5-dimethoxyphenethyl, 4-chlorophenpropyl, 2,4,5-trimethylphenbutyl, 2,4-dichlorophenylbutyl and the like. The term aralkyl also includes $CH_2$-(2-W)aryl where W is defined above.

Halogen or halo is meant to include iodo, fluoro, bromo and chloro moieties.

Because of the C=C or C=N double bonds the novel compounds of the general Formula I may be obtained in preparation as E/Z isomeric mixtures. These isomers can be separated into individual components by conventional means. Both the individual isomeric compounds and mixtures thereof form subjects of the invention and can be used as fungicides.

A preferred embodiment of this invention are the compounds, enantiomorphs, salts and complexes of Formula (I) is when $R_4$ and $R_5$ are hydrogen and $R_2$ is $(C_1-C_{12})$alkyl, $(C_2-C_8)$alkenyl, phenyl or benzyl substituted with preferably two substituents independently selected from halo, trihalomethyl, cyano, $(C_1-C_4)$alkyl, $(C_1-C_4)$alkylthio, $(C_1-C_4)$alkoxy or phenyl, the bond containing $R_4$ and $R_5$ is a double bond and Y is a direct carbon bond and where the $OCH_2$(2-W-aryl) is bonded at the meta position to Y.

A more preferred embodiment of this invention are the compounds, enatiamorphs, salts and complexes of Formula (I) is when $R_4$ and $R_5$ are hydrogen, $R_2$ is methyl, ethyl, allyl or n-propyl and A is CH and V is O. The preferred geometry when A is CH or N is the E isomer.

Typical compounds encompassed by the present invention of formulas II, III, and IV include those compounds presented in tables 1, 2 and 3.

TABLE 1

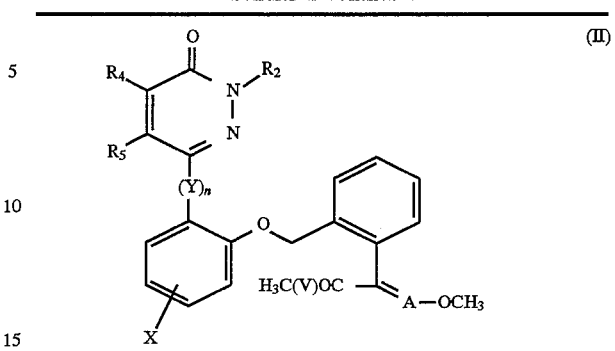

(II)

| Cmpd # | $R_2$ | $R_4$ | $R_5$ | X | A | V | Y | n |
|---|---|---|---|---|---|---|---|---|
| 1 | $CH_3$ | H | H | H | CH | O | — | 0 |
| 2 | $C_2H_5$ | H | H | H | CH | O | — | 0 |
| 3 | $CH_2CH_2CH_3$ | H | H | H | CH | O | — | 0 |
| 4 | $CH(CH_3)_2$ | H | H | H | CH | O | — | 0 |
| 5 | $CH_2CH(CH_3)_2$ | H | H | H | CH | O | — | 0 |
| 6 | $CH_2(CH_2)_3CH_3$ | H | H | H | CH | O | — | 0 |
| 7 | Ar(4Cl) | H | H | H | CH | O | — | 0 |
| 8 | $CH_2Ar(4Cl)$ | H | H | H | CH | O | — | 0 |
| 9 | $CH_2CH_2Ar$ | H | H | H | CH | O | — | 0 |
| 10 | $CH_2CF_3$ | H | H | H | CH | O | — | 0 |
| 11 | $CH_3$ | H | H | H | CH | O | O | 1 |
| 12 | $CH_2CH_3$ | H | H | H | CH | O | O | 1 |
| 13 | $CH_2$cyclopropyl | H | H | H | CH | O | O | 1 |
| 14 | $CH_2CH_2CH_3$ | H | H | H | CH | O | O | 1 |
| 15 | $CH_2CH_3$ | H | H | H | N | O | — | 0 |
| 16 | $CH_2CH_2CH_3$ | H | H | H | N | O | — | 0 |
| 17 | $CH_2CH=CH_2$ | H | H | H | N | O | — | 0 |
| 18 | $CH_2CO_2CH_3$ | H | H | H | N | O | — | 0 |
| 19 | $CH_2CH_2CH_3$ | H | H | H | N | O | O | 1 |
| 20 | $CH_2CH=CH_2$ | H | H | H | N | O | O | 1 |
| 21 | $CH_2CH_2CH=CH_2$ | H | H | H | N | O | O | 1 |
| 22 | $CH_2CH_3$ | H | H | H | N | NH | — | 0 |
| 23 | $CH_2CH_2F$ | H | H | H | N | NH | — | 0 |
| 24 | $CH_2$-cyclo-$C_3H_7$ | H | H | H | N | NH | — | 0 |
| 25 | $CH_2$-1H-1,2,4-triazole | H | H | H | N | NH | — | 0 |
| 26 | $(CH_2)_3Ar$ | H | H | H | N | NH | O | 1 |
| 27 | $CH_2$-(3-pyridinyl) | H | H | H | N | NH | O | 1 |

TABLE 2

(III)

| Cmpd # | $R_2$ | $R_4$ | $R_5$ | X | A | V | Y | n |
|---|---|---|---|---|---|---|---|---|
| 28 | $CH(CH_3)_2$ | H | H | H | CH | O | — | 0 |
| 29 | $CH_2CH(CH_3)_2$ | H | H | H | CH | O | — | 0 |
| 30 | $C(CH_3)_3$ | H | H | H | CH | O | — | 0 |
| 31 | $CH_2(CH_2)_3CH_3$ | H | H | H | CH | O | — | 0 |

TABLE 2-continued

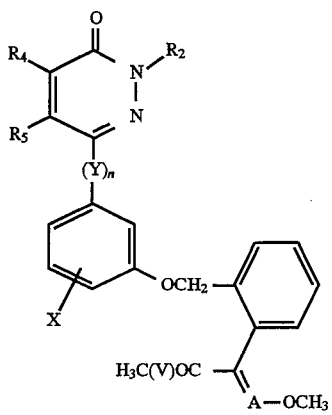

(III)

| Cmpd # | R₂ | R₄ | R₅ | X | A | V | Y | n |
|---|---|---|---|---|---|---|---|---|
| 32 | C(CH₃)CH₂CH₂CH₃ | H | H | H | CH | O | — | 0 |
| 33 | CH₂C(CH₃)₃ | H | H | H | CH | O | — | 0 |
| 34 | CH₂CH₂OCH₂CH₃ | H | H | H | CH | O | — | 0 |
| 35 | CH₂CH(CH₃)OH | H | H | H | CH | O | — | 0 |
| 36 | CH₂CH₂OCOCH₃ | H | H | H | CH | O | — | 0 |
| 37 | CH₂OCOAr | H | H | H | CH | O | — | 0 |
| 38 | CH₂CH₂OCOAr | H | H | H | CH | O | — | 0 |
| 39 | CH₂CH₂Br | H | H | H | CH | O | — | 0 |
| 40 | (CH₂)₂Ar(4Cl) | H | H | H | CH | O | — | 0 |
| 41 | (CH₂)₂Ar(4Cl) | H | H | 3'Cl | CH | O | — | 0 |
| 42 | (CH₂)₃Ar(4Cl) | H | H | H | CH | O | — | 0 |
| 43 | (CH₂)₄Ar | H | H | H | CH | O | — | 0 |
| 44 | (CH₂)₂OAr | H | H | H | CH | O | — | 0 |
| 45 | CH₂C(Cl)=CH₂ | H | H | H | CH | O | — | 0 |
| 46 | CH₂CCH | H | H | H | CH | O | — | 0 |
| 47 | CH₂CH₂OAr | H | H | 3'-OMe | CH | O | — | 0 |
| 48 | CH₂OCH₂Ar | H | H | H | CH | O | — | 0 |
| 49 | CH₂CH₂OCH₂Ar | H | H | H | CH | O | — | 0 |
| 50 | CH₂CH=CHAr | H | H | H | CH | O | — | 0 |
| 51 | 2-pyridinyl | H | H | H | CH | O | — | 0 |
| 52 | 4-pyridinyl | H | H | H | CH | O | — | 0 |
| 53 | 2-pyrimidinyl | H | H | H | CH | O | — | 0 |
| 54 | 4-pyrimidinyl | H | H | H | CH | O | — | 0 |
| 55 | CH₂-(2-pyridinyl) | H | H | H | CH | O | — | 0 |
| 56 | CH₂-(3-pyridinyl) | H | H | H | CH | O | — | 0 |
| 57 | CH₂-pyrazinyl | H | H | H | CH | O | — | 0 |
| 58 | CH₂-(2-thienyl) | H | H | H | CH | O | — | 0 |
| 59 | CH₂-(3-thienyl) | H | H | H | CH | O | — | 0 |
| 60 | CH₂-(1-morpholinyl) | H | H | H | CH | O | — | 0 |
| 61 | CH₂-(1-piperidinyl) | H | H | H | CH | O | — | 0 |
| 62 | CH₂-(2-furyl) | H | H | H | CH | O | — | 0 |
| 63 | CH₂-epoxide | H | H | H | CH | O | — | 0 |
| 64 | CH₂—Si(CH₃)₃ | H | H | H | CH | O | — | 0 |
| 65 | CH₂—Si(CH₃)₂-t-butyl | H | H | H | CH | O | — | 0 |
| 66 | CH₂—Si(CH₃)₂Ar | H | H | H | CH | O | — | 0 |
| 67 | CH₂—PO(OCH₃)₂ | H | H | H | CH | O | — | 0 |
| 68 | CH₂—PO(OC₂H₅)₂ | H | H | H | CH | O | — | 0 |
| 69 | CH₂OSO₂CH₃ | H | H | H | CH | O | — | 0 |
| 70 | CH₂OSO₂Ar | H | H | H | CH | O | — | 0 |
| 71 | CH₂-(4-CF₃-pyridin-2-yl) | H | H | H | CH | O | — | 0 |
| 72 | CH₂-(1-napthyl) | H | H | H | CH | O | — | 0 |
| 73 | CH₂-(2-napthyl) | H | H | H | CH | O | — | 0 |
| 74 | CH₂—CO₂C₂H₅ | H | H | H | CH | O | — | 0 |
| 75 | CH₂—CH=CH—CO₂CH₃ | H | H | H | CH | O | — | 0 |
| 76 | CH₂CH₂CN | H | H | H | CH | O | — | 0 |
| 77 | CH₂—CH=C(CH₃)₂ | H | H | H | CH | O | — | 0 |
| 78 | CH₂—C(CH₃)=CHCH₃ | H | H | H | CH | O | — | 0 |
| 79 | CH₂—C(CH₃)=C(CH₃)₂ | H | H | H | CH | O | — | 0 |
| 80 | C₂H₅ | CH₃ | CH₃ | H | CH | O | — | 0 |
| 81 | CH₂CH₂CH₃ | CH₃ | CH₃ | H | CH | O | — | 0 |
| 82 | CH₂CF₃ | CH₃ | CH₃ | H | CH | O | — | 0 |
| 83 | CH₂CH(CH₃)₂ | CH₃ | CH₃ | H | CH | O | — | 0 |
| 84 | C(CH₃)₃ | CH₃ | CH₃ | H | CH | O | — | 0 |
| 85 | CH₂(CH₂)₃CH₃ | CH₃ | CH₃ | H | CH | O | — | 0 |
| 86 | CH(CH₃)(CH₂)₂CH₃ | CH₃ | CH₃ | H | CH | O | — | 0 |
| 87 | (CH₂)₂C(CH₃)₂ | CH₃ | CH₃ | H | CH | O | — | 0 |
| 88 | CH₂C(CH₃)₃ | CH₃ | CH₃ | H | CH | O | — | 0 |

TABLE 2-continued (III)

| Cmpd # | R$_2$ | R$_4$ | R$_5$ | X | A | V | Y | n |
|---|---|---|---|---|---|---|---|---|
| 89 | C$_2$H$_5$ | H | H | 3'Cl | CH | O | — | 0 |
| 90 | CH$_2$CH$_2$CH$_3$ | H | H | 3'OCH$_3$ | CH | O | — | 0 |
| 91 | CH(CH$_3$)$_2$ | H | H | 3'Cl | CH | O | — | 0 |
| 92 | CH$_2$CH(CH$_3$)$_2$ | H | H | 3'OCH$_3$ | CH | O | — | 0 |
| 93 | C(CH$_3$)$_3$ | H | H | 3'Cl | CH | O | — | 0 |
| 94 | CH$_2$(CH$_2$)$_3$CH$_3$ | H | H | 3'OCH$_3$ | CH | O | — | 0 |
| 95 | C(CH$_3$)CH$_2$CH$_2$CH$_3$ | H | H | 3'Cl | CH | O | — | 0 |
| 96 | (CH$_2$)$_2$CH(CH$_3$)$_2$ | H | H | 3'OCH$_3$ | CH | O | — | 0 |
| 97 | CH$_2$C(CH$_3$)$_3$ | H | H | 3'Cl | CH | O | — | 0 |
| 98 | CH$_2$CCH | H | H | 3'OCH$_3$ | CH | O | — | 0 |
| 99 | CH(CH$_3$)$_2$ | H | H | H | CH | O | O | 1 |
| 100 | CH$_2$CH(CH$_3$)$_2$ | H | H | H | CH | O | O | 1 |
| 101 | CH$_2$CF$_3$ | H | H | H | CH | O | O | 1 |
| 102 | CH$_2$(CH$_2$)$_3$CH$_3$ | H | H | H | CH | O | O | 1 |
| 103 | CH(CH$_3$)CH$_2$CH$_2$CH$_3$ | H | H | H | CH | O | O | 1 |
| 104 | (CH$_2$)$_2$CH(CH$_3$)$_2$ | H | H | H | CH | O | O | 1 |
| 105 | CH$_2$C(CH$_3$)$_3$ | H | H | H | CH | O | O | 1 |
| 106 | CH$_2$CH$_2$OH | H | H | H | CH | O | O | 1 |
| 107 | CH$_2$CH(CH$_3$)OH | H | H | H | CH | O | O | 1 |
| 108 | CH$_2$CH$_2$F | H | H | H | CH | O | O | 1 |
| 109 | CH$_2$CH$_2$Cl | H | H | H | CH | O | O | 1 |
| 110 | CH$_2$CH$_2$Br | H | H | H | CH | O | O | 1 |
| 111 | (CH$_2$)$_2$Ar | H | H | H | CH | O | O | 1 |
| 112 | (CH$_2$)$_2$Ar(4Cl) | H | H | H | CH | O | O | 1 |
| 113 | (CH$_2$)$_3$Ar | H | H | H | CH | O | O | 1 |
| 114 | (CH$_2$)$_2$OAr | H | H | H | CH | O | O | 1 |
| 115 | CH$_2$-(2-pyridinyl) | H | H | H | CH | O | O | 1 |
| 116 | CH$_2$-(3-pyridinyl) | H | H | H | CH | O | O | 1 |
| 117 | CH$_2$-pyrazinyl | H | H | H | CH | O | O | 1 |
| 118 | CH$_2$-(2-thienyl) | H | H | H | CH | O | O | 1 |
| 119 | CH$_2$-(3-thienyl) | H | H | H | CH | O | O | 1 |
| 120 | CH$_2$-(1-morpholinyl) | H | H | H | CH | O | O | 1 |
| 121 | CH$_2$-(1-piperidinyl) | H | H | H | CH | O | O | 1 |
| 122 | CH$_2$-(3-pyrimidinyl) | H | H | H | CH | O | O | 1 |
| 123 | CH$_2$C(Cl)=CH$_2$ | H | H | H | CH | O | O | 1 |
| 124 | CH$_2$CCH | H | H | H | CH | O | O | 1 |
| 125 | CH$_2$-cyclo-C$_5$H$_9$ | H | H | H | CH | O | O | 1 |
| 126 | CH$_2$CH$_2$OCH$_2$Ar | H | H | H | CH | O | O | 1 |
| 127 | CH$_2$CH=CHAr | H | H | H | CH | O | O | 1 |
| 128 | CH$_2$-1H-1,2,4-triazole | H | H | H | CH | O | O | 1 |
| 129 | CH$_2$-(3-pyridinyl) | H | H | H | CH | O | O | 1 |
| 130 | CH$_2$-(1-morpholinyl) | H | H | H | CH | O | O | 1 |
| 131 | CH$_3$ | H | H | H | CH | O | CH$_2$ | 1 |
| 132 | CH$_2$CH$_3$ | H | H | H | CH | O | CH$_2$ | 1 |
| 133 | CH$_2$CH$_2$CH$_3$ | H | H | H | CH | O | CH$_2$ | 1 |
| 134 | CH$_3$ | H | H | H | CH | O | NCH$_3$ | 1 |
| 135 | CH$_2$CH$_3$ | H | H | H | CH | O | NCH$_3$ | 1 |
| 136 | CH$_2$CH$_2$CH$_3$ | H | H | H | CH | O | NCH$_3$ | 1 |
| 137 | CH$_2$CH$_3$ | H | H | H | CH | O | S | 1 |
| 138 | CH$_2$CH$_2$F | H | H | H | CH | O | S | 1 |
| 139 | CH$_2$CH=CH$_2$ | H | H | H | CH | O | S | 1 |
| 140 | CH$_2$-1H-1,2,4-triazole | H | H | H | CH | O | S | 1 |
| 141 | CH$_2$-(3-pyridinyl) | H | H | H | CH | O | S | 1 |
| 142 | CH$_2$-(1-morpholinyl) | H | H | H | CH | O | S | 1 |
| 143 | CH$_2$CH$_3$ | H | H | H | N | O | — | 0 |
| 144 | CH$_2$CF$_3$ | H | H | H | N | O | — | 0 |
| 145 | CH$_2$CH$_2$CH$_3$ | H | H | H | N | O | — | 0 |

TABLE 2-continued

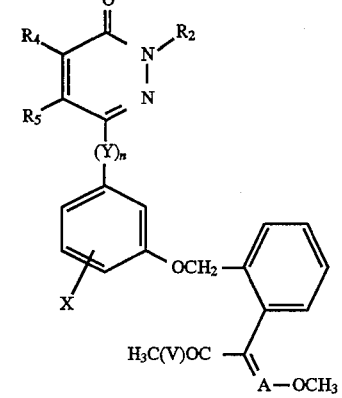

(III)

| Cmpd # | $R_2$ | $R_4$ | $R_5$ | X | A | V | Y | n |
|---|---|---|---|---|---|---|---|---|
| 146 | $CH_2CH(CH_3)_2$ | H | H | H | N | O | — | 0 |
| 147 | $C(CH_3)_3$ | H | H | H | N | O | — | 0 |
| 148 | $CH_2(CH_2)_3CH_3$ | H | H | H | N | O | — | 0 |
| 149 | $CH_2CH_2F$ | H | H | H | N | O | — | 0 |
| 150 | $CH_2CH_2Cl$ | H | H | H | N | O | — | 0 |
| 151 | $(CH_2)_2Ar$ | H | H | H | N | O | — | 0 |
| 152 | $(CH_2)_2Ar(4Cl)$ | H | H | H | N | O | — | 0 |
| 153 | $(CH_2)_3Ar$ | H | H | H | N | O | — | 0 |
| 154 | $(CH_2)_2OAr$ | H | H | H | N | O | — | 0 |
| 155 | $CH_2CCH$ | H | H | H | N | O | — | 0 |
| 156 | $CH_2$-1H-1,2,4-triazole | H | H | H | N | O | — | 0 |
| 157 | $CH_2$-(3-pyridinyl) | $CH_3$ | $CH_3$ | H | N | O | — | 0 |
| 158 | $CH(CH_3)_2$ | H | H | H | N | O | O | 1 |
| 159 | $CH_2CH(CH_3)_2$ | H | H | H | N | O | O | 1 |
| 160 | $C(CH_3)_3$ | H | H | H | N | O | O | 1 |
| 161 | $CH_2(CH_2)_3CH_3$ | H | H | H | N | O | O | 1 |
| 162 | $CH_2CH_3$ | H | H | H | N | O | S | 1 |
| 163 | $CH_2CH_3$ | H | H | H | N | O | $CH_2$ | 1 |
| 164 | $CH_2CH_3$ | H | H | H | N | O | $NCH_3$ | 1 |
| 165 | $CH_2CH_3$ | H | H | H | N | NH | — | 0 |
| 166 | $CH_2CH=CH_2$ | H | H | H | N | NH | — | 0 |
| 167 | $CH_2CH_2CH_3$ | H | H | H | N | NH | — | 0 |
| 168 | $CH_2CH(CH_3)_2$ | H | H | H | N | NH | — | 0 |
| 169 | $C(CH_3)_3$ | H | H | H | N | NH | — | 0 |
| 170 | $CH_2(CH_2)_3CH_3$ | H | H | H | N | NH | — | 0 |
| 171 | $CH_2CCH$ | H | H | H | N | NH | — | 0 |
| 172 | $CH_2$-cyclo-$C_5H_9$ | H | H | H | N | NH | — | 0 |
| 173 | $CH_2CH_2OCH_2Ar$ | H | H | H | N | NH | — | 0 |
| 174 | $CH_2CH=CHAr$ | H | H | H | N | NH | — | 0 |
| 175 | $CH_2$-1H-1,2,4-triazole | H | H | H | N | NH | — | 0 |
| 176 | $CH_2$-(3-pyridinyl) | H | H | H | N | NH | — | 0 |
| 177 | $CH_2$-(1-morpholinyl) | H | H | H | N | NH | — | 0 |
| 178 | $CH_3$ | H | H | H | N | NH | O | 1 |
| 179 | $CH_2CH_3$ | H | H | H | N | NH | O | 1 |
| 180 | $CH_2CH_2CH_3$ | H | H | H | N | NH | O | 1 |
| 181 | $CH(CH_3)_2$ | H | H | H | N | NH | O | 1 |
| 182 | $CH_2CH(CH_3)_2$ | H | H | H | N | NH | O | 1 |
| 183 | $CH_2CH_2F$ | H | H | H | N | NH | O | 1 |
| 184 | $CH_2CH_2Cl$ | H | H | H | N | NH | O | 1 |
| 185 | $CH_3$ | H | H | H | N | NH | S | 1 |

TABLE 3

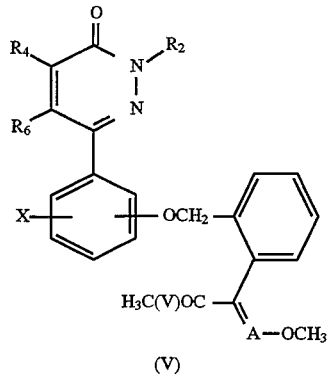

(IV)

| Cmpd # | R₂ | R₄ | R₅ | X | A | V | Y | n |
|---|---|---|---|---|---|---|---|---|
| 186 | CH₃ | H | H | H | CH | O | — | 0 |
| 187 | CH₂CH₃ | H | H | H | CH | O | — | 0 |
| 188 | CH₂CH₂CH₃ | H | H | H | CH | O | — | 0 |
| 189 | CH(CH₃)₂ | H | H | H | CH | O | — | 0 |
| 190 | CH₂CH(CH₃)₂ | H | H | H | CH | O | — | 0 |
| 191 | CH₂CH₂F | H | H | H | CH | O | — | 0 |
| 192 | CH₂CH₂Cl | H | H | H | CH | O | — | 0 |
| 193 | CH₃ | H | H | H | CH | O | — | 0 |
| 194 | CH₂CH₃ | H | H | H | CH | O | — | 0 |
| 195 | CH₂CH₂CH₃ | H | H | H | CH | O | — | 0 |
| 196 | CH₃ | H | H | H | CH | O | O | 1 |
| 197 | CH₂CH₃ | H | H | H | CH | O | O | 1 |
| 198 | CH₂CH₂CH₃ | H | H | H | CH | O | O | 1 |
| 199 | CH₂(CH₂)₂CH₃ | H | H | H | CH | O | O | 1 |
| 200 | CH₂CH₂F | H | H | H | CH | O | O | 1 |
| 201 | CH₃ | H | H | H | CH | O | S | 1 |
| 202 | CH₂CH₃ | H | H | H | CH | O | S | 1 |
| 203 | CH₂CH=CH₂ | H | H | H | CH | O | S | 1 |
| 204 | CH₃ | H | H | H | N | O | — | 0 |
| 205 | CH₂CH₃ | H | H | H | N | O | O | 1 |
| 206 | CH₂CH₂CH₃ | H | H | H | N | O | — | 0 |
| 207 | CH₂(CH₂)₂CH₃ | H | H | H | N | O | O | 1 |
| 208 | CH₂CH₂F | H | H | H | N | O | — | 0 |
| 209 | CH₂CH=CH₂ | H | H | H | N | O | O | 1 |
| 210 | CH₂CH₂OCOCH₃ | H | H | H | N | O | — | 0 |
| 211 | CH₂-(2-pyridinyl) | H | H | H | N | O | O | 1 |
| 212 | CH₃ | H | H | H | N | NH | — | 0 |
| 213 | CH₂CH₃ | H | H | H | N | NH | O | 1 |
| 214 | CH₂CH₂CH₃ | H | H | H | N | NH | — | 0 |
| 215 | CH₂(CH₂)₂CH₃ | H | H | H | N | NH | O | 1 |
| 216 | CH₂CH₂F | H | H | H | N | NH | — | 0 |
| 217 | CH₂CH=CH₂ | H | H | H | N | NH | S | 1 |
| 218 | CH₂CH₂OCOCH₃ | H | H | H | N | NH | — | 0 |

As used in Tables 1, 2, and 3 Ar is understood to be phenyl.

The pyridazinones and dihydropyridazinones of the of the present invention may be prepared by conventional synthetic routes. For example, pyridazinones of Fomula (I), when n is 0 as in Formula (V) and A and V are as defined in Formula (I), are prepared by alkylation of the 6-(hydroxy)phenyl-2, 4,5-trisubstituted-pyridazin-3-one (VI) as shown in scheme A:

Scheme A:

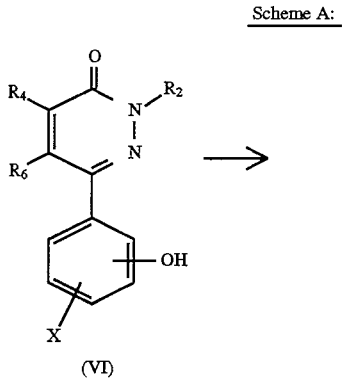

(VI)

-continued
Scheme A:

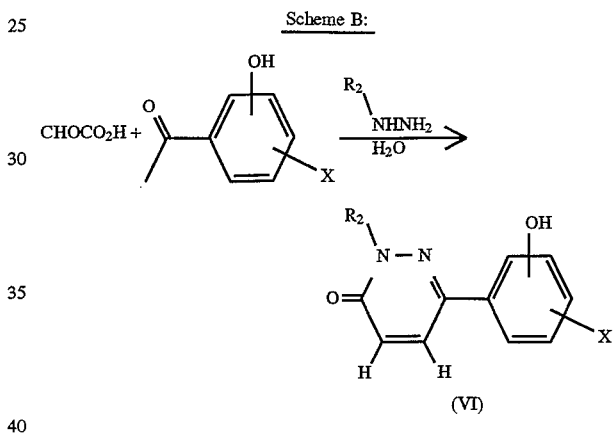

(V)

4,5,6-trisubstituted-3(2H)-pyridazinones (VI) and 4,5-dihydropyridazinones can be prepared as described in EP 308404. Specifically 6-(hydroxyphenyl)-2-substituted-pyridazin-3-ones (VI, where R₄=R₅=H) are prepared as shown in Scheme B.

Scheme B:

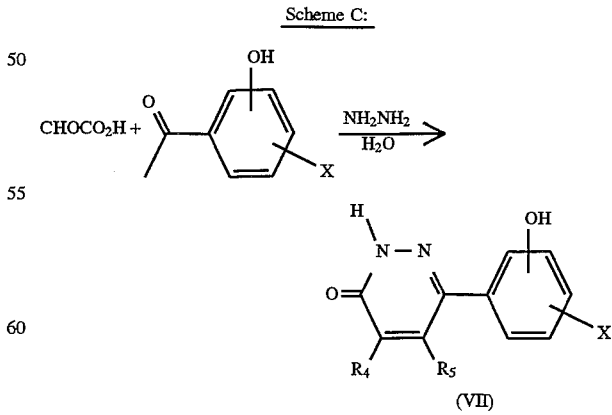

(VI)

Alternatively, hydroxyacetophenones and glyoxalic acid can be treated with hydrazine to afford the 6-(hydroxyphenyl)-3(2H)-pyridazinone (VII) as shown in Scheme C. 2-, 3- or 4-hydroxyacetophenone can be utilized in the condensation which provides the isomeric 6-(hydroxyphenyl)pyridazinones (VI and VII).

Scheme C:

(VII)

The pyridazinone (VII) is alkylated with R₂X under basic conditions such as NaH in DMF, potassium hydroxide in DMSO or potassium carbonate in DMF or acetone, and provides a mixture of N and O alkylated products as shown in Scheme D. The nitrogen monoalkyated product (VI) can be separated by conventional chromatographic techniques and treated with 2-W-benzylbromide to provide (V) or a mixture of (VI) and (VIII) can be alkylated with the benzyl bromide, in situ (without isolation of (VI) or (VII)), after which (V) is separated by chromatography from unreacted (VIII).

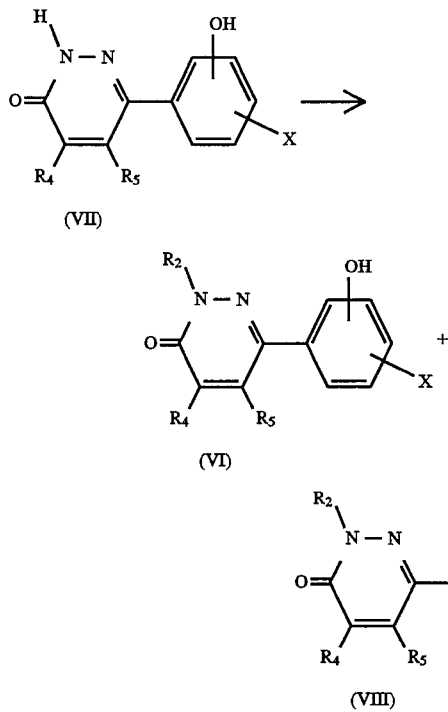

The reaction of pyridazinones (VI) with methyl E-α-(2-bromomethylphenyl)-β-methoxyacrylate is carried out in the presence of a base such as a metal hydride, preferably NaH, in an aprotic solvent such as N,N-dimethyl-formamide and provides compounds of Formula (V) where A is CH and V is oxygen. Methyl E-α-(2-bromo methylphenyl)-β-methoxyacrylate, as a single E isomer, can be prepared in two steps from 2-methylphenylacetate as described previously in U.S. Pat. No. 4,914,128. Alternatively, the pyridazinone (VI) can be reacted with methyl 2-(bromomethyl) phenyl glyoxylate followed by Wittig condensation with methoxymethyltriphenyl phosphorane as described in EP 348766, EP178826 and DE 3705389.

Compounds of Formula (V) where A is N and V is oxygen are prepared from pyridazinones (VI) by the reaction with methyl E-2-(bromomethyl)phenylglyoxylate O-methyloxime in the presence of a base such as a metal hydride, preferably NaH, in an aprotic solvent such as N,N-dimethylformamide. Methyl 2-(bromomethyl)phenyl glyoxylate O-methyloxime can be prepared as described in U.S. Pat. Nos. 4,999,042 and 5,157,144. Methyl 2-methylphenylacetate is treated with an alkyl nitrite under basic conditions to provide after methylation, methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride. Alternatively when A is N and V is oxygen, pyridazinone (VI) can be reacted with methyl 2-(bromomethyl)-phenylglyoxylate followed by reaction with methoxylamine HCl or hydroxylamine HCl followed by methylation.

The amminolysis of oximinoacetates to oximinoacetamides has been described in U.S. Pat. Nos. 5,185,342, 5,221,691 and 5,194,662. Compounds of Formula (V) where A is N and V is O are treated with 40% aqueous methylamine in methanol to provide compounds of Formula (V) where V is NH(CH₃). Alternatively, pyridazinone (VI) is reacted with N-methyl E-2-methoxyimino-2-[2-(bromomethyl)phenyl]acetamide in the presence of a base such as a metal hydride, preferably NaH, in an aprotic solvent such as dimethyl formide (DMF). N-methyl E-2-methoxyimino-2-[2-(bromomethyl) phenyl]acetamide is described in WO 9419331.

Compounds of Formula (I) where n=1, and more specifically, Y is oxygen are prepared as is shown in Scheme E.

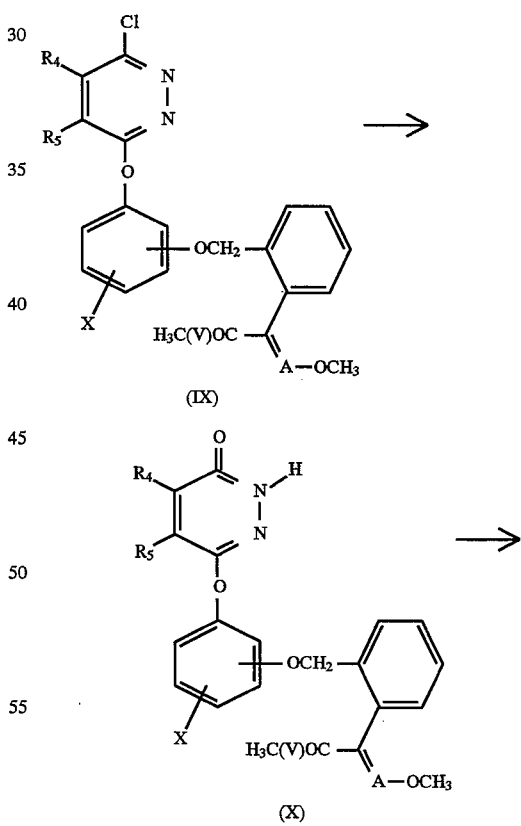

15
-continued
Scheme E:

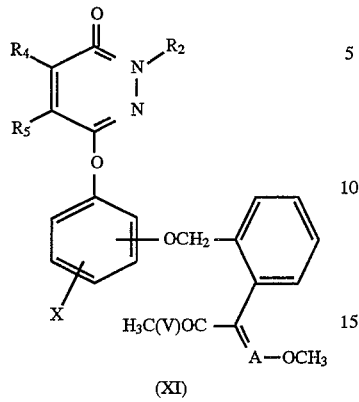

(XI)

The alkylation of (X) with R₂X proceeds under basic conditions similiar to those described for (VII). The 6-((2'-(W)benzyloxy)phenoxy)-4,5-disubstituted-3(2H)-pyridazinone (X) is prepared by acidic hydrolysis of the 6-((2'-(W)benzyloxy)phenoxy))-4,5-disubstituted-3-chloropyridazine (IX) which is prepared by alkylation of phenolicintermediate (XII), as shown in Scheme F, with various benzylic bromides under conditions similiar to the conversion of (VI) to (V). The various alkylating reagents provide for when, A is CH or N and V are oxygen and NH. The 6-(hydroxyphenoxy)-4,5-disubstituted-3-chloropyridazine (XII) is prepared by the reaction of dichloropyridazine with dihydroxybenzene, such as resorcinol and catechol as shown in Scheme F.

Scheme F:

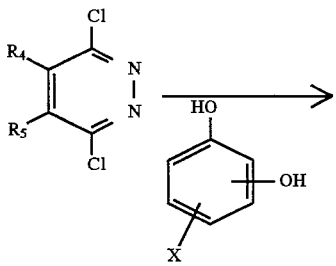

16
-continued
Scheme F:

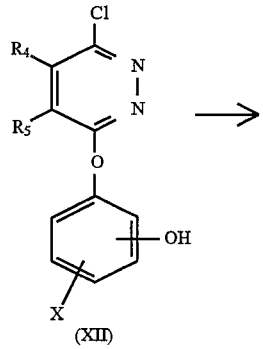

(XII)

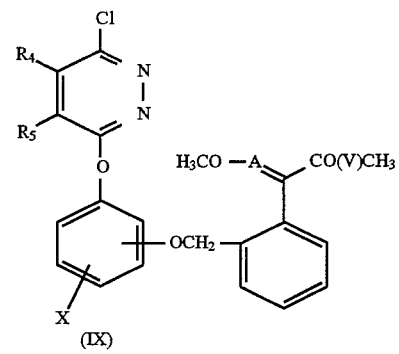

(IX)

Compounds of Formula (I) wherein Y is S or N—R₆ can be prepared in an analogous sequence as described in Scheme F. When Y is S, substituted mercaptophenols are utilized, likewise when Y is N—R₆, substituted aminophenols are utilized.

The following examples in Table 4 are provided to illustrate the present invention.

TABLE 4

| Cmpd # | FORMULA | R₂ | R₄ | R₅ | X | A | V | Y | n |
|---|---|---|---|---|---|---|---|---|---|
| 219 | II | CH₂CCCH₂CH₃ | H | H | H | CH | O | — | 0 |
| 220 | II | C₂H₅ | H | H | H | CH | O | — | 0 |
| 221 | II | CH₂CCCH₂CH₃ | H | H | 3'-OCH₃ | CH | O | — | 0 |
| 222 | II | CH₂CCCH₂CH₃ | H | H | 3'-Cl | CH | O | — | 0 |
| 223 | III | CH₂CCCH₂CH₃ | H | H | H | CH | O | — | 0 |
| 224 | III | CH₂CO₂CH₃ | H | H | H | CH | O | — | 0 |
| 225 | II | CH₂Ar | H | H | 3'-OCH₃ | CH | O | — | 0 |
| 226 | II | CH₂Ar | H | H | H | CH | O | — | 0 |
| 227 | III | CH₃ | H | H | H | CH | O | — | 0 |
| 228 | III | CH₂Ar | H | H | H | CH | O | — | 0 |
| 229 | IV | CH₂CCCH₂CH₃ | H | H | H | CH | O | — | 0 |
| 230 | III | CH₂CH=CH₂ | H | H | H | CH | O | — | 0 |
| 231 | III | C₂H₅ | H | H | H | CH | O | — | 0 |
| 232 | III | n-C₃H₇ | H | H | H | CH | O | — | 0 |
| 233 | III | CH₂CH₂CN | H | H | H | CH | O | — | 0 |
| 234 | III | CH₂CH₂CH=CH₂ | H | H | H | CH | O | — | 0 |
| 235 | III | CH₂CH₂OCH₃ | H | H | H | CH | O | — | 0 |
| 236 | III | Ar | H | H | H | CH | O | — | 0 |
| 237 | III | CH₃ | H | H | H | CH | O | O | 1 |
| 238 | III | CH₂CH₂F | H | H | H | CH | O | — | 0 |
| 239 | III | CH₃ | H | H | H | N | O | — | 0 |
| 240 | III | CH₂COAr | H | H | H | CH | O | — | 0 |
| 241 | III | CH₃ | H | H | H | N | NH | — | 0 |
| 242 | III | CH₂cyclopropyl | H | H | H | CH | O | — | 0 |
| 243 | III | CH₂(2-napthyl) | H | H | H | CH | O | — | 0 |
| 244 | III | CH₂CF₃ | H | H | H | CH | O | — | 0 |
| 245 | III | Ar(3Cl) | H | H | H | CH | O | — | 0 |
| 246 | III | Ar(2Cl) | H | H | H | CH | O | — | 0 |
| 247 | III | CH₃ | H | H | 3'-OCH₃ | CH | O | — | 0 |
| 248 | III | CH₂Ar | H | H | H | CH | O | O | 1 |
| 249 | III | CH₂CH=CH₂ | H | H | H | CH | O | O | 1 |
| 250 | III | CH₂CCCH₂CH₃ | H | H | H | CH | O | O | 1 |
| 251 | III | n-C₃H₇ | H | H | H | CH | O | O | 1 |
| 252 | III | H | H | H | H | CH | O | O | 1 |
| 253 | III | n-C₄H₉ | H | H | H | CH | O | — | 0 |
| 254 | III | sec-C₄H₉ | H | H | H | CH | O | — | 0 |
| 255 | III | CF₂-(5'-Cl-2-thienyl) | H | H | H | CH | O | — | 0 |
| 256 | III | (CH₂)₂-(1-morpholino) | H | H | H | CH | O | — | 0 |
| 257 | III | (CH₂)₃-Ar | H | H | H | CH | O | — | 0 |
| 258 | III | CH₂-Ar(2Cl) | H | H | H | CH | O | — | 0 |
| 259 | III | CH₂-Ar(3Cl) | H | H | H | CH | O | — | 0 |
| 260 | III | CH₂-Ar(4Cl) | H | H | H | CH | O | — | 0 |
| 261 | III | CH₂-cyclohexyl | H | H | H | CH | O | — | 0 |
| 262 | III | H | H | H | H | CH | N | O | 1 |
| 263 | III | CH₂Ar | H | H | H | CH | N | O | 1 |
| 264 | III | CH₂CCCH₂CH₃ | H | H | H | CH | N | O | 1 |
| 265 | III | CH₂CH=CH₂ | H | H | H | CH | N | O | 1 |
| 266 | III | CH₂CH₂CH₃ | H | H | H | CH | N | O | 1 |
| 267 | III | CH₂CO₂CH₂Ar | H | H | H | CH | O | — | 0 |
| 268 | III | (CH₂)₃OAr | H | H | H | CH | O | — | 0 |
| 269 | III | CH₂CH(CH₂CH₃)₂ | H | H | H | CH | O | — | 0 |
| 270 | III | CH₂-1H-1,2,4-triazole | H | H | H | CH | O | — | 0 |
| 271 | III | CH₂CH₂Ar | H | H | H | CH | O | — | 0 |
| 272 | III | CH₂CH₂OH | H | H | H | CH | O | — | 0 |
| 273 | III | CH₂CH₂Cl | H | H | H | CH | O | — | 0 |

TABLE 4-continued

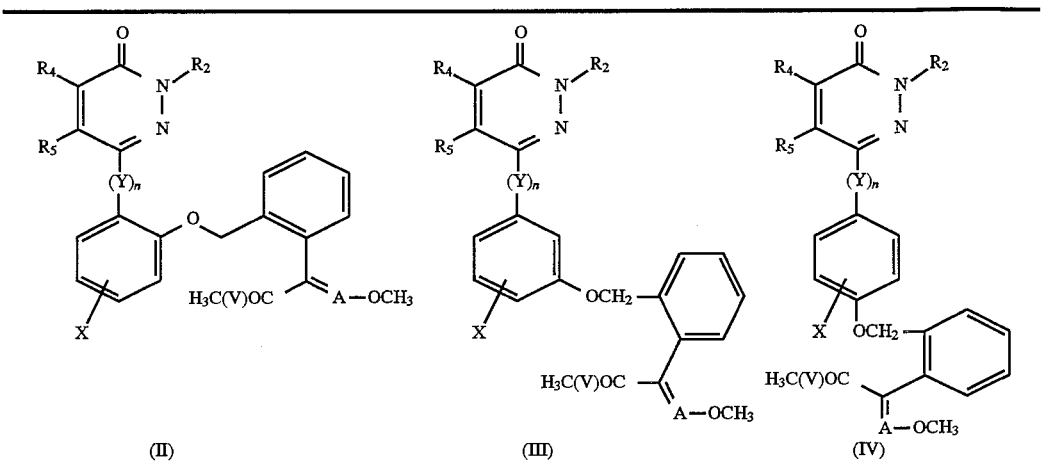

| Cmpd # | FORMULA | R₂ | R₄ | R₅ | X | A | V | Y | n |
|---|---|---|---|---|---|---|---|---|---|
| 274 | III | CH=CH₂ | H | H | H | CH | O | — | 0 |
| 275 | III | CH₂CH₂CH(CH₃)₂ | H | H | H | CH | O | — | 0 |
| 276 | III | CH₂CH=CHCH₃ | H | H | H | CH | O | — | 0 |
| 277 | III | CH₂CH=C(CH₃)₂ | H | H | H | CH | O | — | 0 |
| 278 | II | H | H | H | H | CH | O | O | 1 |
| 279 | II | CH₂CH=CH₂ | H | H | H | CH | O | O | 1 |
| 280 | II | CH₂CCCH₂CH₃ | H | H | H | CH | O | O | 1 |

Ex. 281

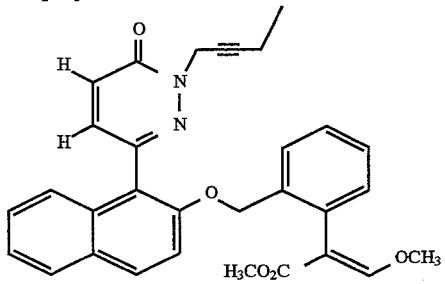

Ex. 282

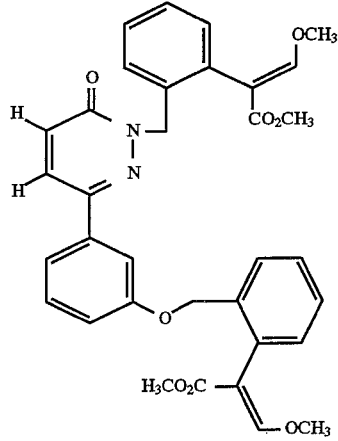

As used in Table 4, Ar is understood to be phenyl.

The compounds of this invention can be made according to the the following procedures:

EXAMPLE 1

Methyl α-[2-(3-(2'-(2'',2'',2''-Trifluoroethyl) pyridazin-3'-on-6'-yl)phenyl)oxymethylphenyl]-β-methoxyacrylate. (Table 4; Compound 244)

A 500 ml round bottom flask is equipped with a magnetic stirrer and was charged with 0.95 g (3.51 mmoles) of 6-(3-hydroxyphenyl)-2-(2',2',2'-trifluoroethyl)-3(2H)-pyridazinone and 20 mls of dimethylformamide (DMF). To this solution was added 0.23 g (3.51 mmoles) of powdered 87% potassium hydroxide, followed by 1.0 g of methyl α-(2-bromomethylphenyl)-β-methoxyacrylate. The reaction was stirred at ambient temperature for a total of 18 hours, then poured into 100 mls of water and extracted with ethyl acetate (3×100 mls). The ethyl acetate extract was then washed with 100 mls of water and 100 mls of saturated sodium chloride solution, dried over anhydrous magnesium sulfate, and filtered. The filtrate was concentrated by evaporation under reduced pressure to afford 1.4 g of a yellow liquid which was chromatographed on a mixed bed of neutral alumina and silica gel with 100% ethyl acetate. The pure fractions were combined to yield 1.1 g of methyl α-[2-(3-(2'-(2",2",2"-trifluoroethyl)pyridazin-3'-on-6'-yl) phenyl)oxymethylphenyl]-β-methoxy acrylate as a thick yellow oil.

EXAMPLE 2

Methyl α-[2-(3-(2'-(2"-Fluoroethyl)pyridazin-3'-on-6'-yl)phenyl)oxymethylphenyl]-β-methoxyacrylate.
(Table 4; Compound 238)

A 500 ml round bottom flask was equipped with magnetic stirrer and was charged with 1.0 g (5.32 mmoles) of 6-(3-hydroxyphenyl)-3(2H)-pyridazinone, 0.74 g (5.32 mmoles) of potassium carbonate, and 20 mls of DMF. To this mixture was added 0.67 g (5.32 mmoles) of 1-bromo-2-fluoroethane. The reaction was then stirred at ambient temperature for a total of 20 hours, followed by the addition of 0.35 g (5.32 mmoles) of powdered 87% KOH and 1.5 g of methyl α-(2-bromomethylphenyl)-β-methoxyacrylate (5.32 mmoles) The reaction was stirred at ambient temperature for a total of 18 hours, then poured into 100 mls of water and extracted with ethyl acetate (3×100 mls). The ethyl acetate extract was then washed with 100 mls of water and 100 mls of saturated sodium chloride solution, dried over anhydrous magnesium sulfate, and filtered. The filtrate was concentrated by evaporation under reduced pressure to afford 1.2 g of a red liquid which was chromatographed on a mixed bed of neutral alumina and silica gel with 100% ethyl acetate. The pure fractions were combined to yield 0.4 g of methyl α-[2-(3-(2'-(2"-fluoroethyl)pyridazin-3'-on-6'-yl)phenyl) oxymethylphenyl]-β-methoxy-acrylate as a thick yellow oil.

EXAMPLE 3

Preparation of 6-(3-Hydroxyphenyl)-3(2H)-pyridazinone. (Used to Make the Compound of Example 2)

A 500 ml round bottom flask was equipped with a magnetic stirrer, thermometer, addition funnel, and pH electrode and was charged with 18.4 g (0.2 moles) of glyoxylic acid monohydrate and 75 mls of water. The solution was cooled to 10° C. and 20% aqueous potassium hydroxide was added raise the to pH to 8. A partial solution of 3'-hydroxyacetophenone (27.2 g, 0.2 moles) in KOH solution (20 g, 0.36 moles) was added all at once to the cold sodium glyoxylate solution and the reaction was stirred at room temperature for 2 hours. The dark brown solution was then re-cooled to 10° C., and acetic acid was added to pH 8. The contents were transferred to a separatory funnel, and the aqueous solution was extracted with 4×100 mls of methylene chloride to remove any unreacted 3'-hydroxyacetophenone. The aqueous fraction was again transferred to the reaction flask, cooled to 10° C. and further treated with acetic acid to pH 4.5, then concentrated ammonium hydroxide was added to pH 8. The solution was then heated under reflux with hydrazine monohydrate (10 mls, 0.2 moles) for 2 hours, then cooled to afford a yellow solid which was collected by vacuum filtration, and washed with water. The product was dried overnight under vacuum at 40° C., to yield 25.2 g of 6-(3-hydroxyphenyl)-3(2H)-pyridazinone (90.6% yield).

NMR (200 MHz, $d_6$-DMSO): 6.9(m, 1H), 7.0(d, 1H), 7.4(m,3H), 8.0(d,1H), 9.8(br s,1H), and 13.2 (br s,1H).

EXAMPLE 4

Preparation of 6-(3-Hydroxyphenyl)-2-(2',2',2'-trifluoroethyl)-3(2H)-pyridazinone. (Used to Make the Compound of Example 1)

Same as Example 3 except 70% 2,2,2-trifluoroethyl hydrazine was employed.

NMR (200 MHz, $d_6$-DMSO): 5.0(q,2H), 6.9(m,1H), 7.1 (d, 1H), 7.3(m,3H0, and 8.0(d, 1H)

EXAMPLE 5

Methyl α-[2-(3-(3(2H)-pyridazin-3'-on-6'-yloxy) phenyl)oxymethylphenyl]-β-methoxyacrylate.
(Table 4; Compound 252)

A 500 ml 3-neck round bottom flask was charged with 9.3 g of methyl α-[2-(3-(3'-chloropyridazin-6'-yl oxy)phenyl) oxymethylphenyl]-β-methoxyacrylate (1.0 eq., 0.022 moles), 5.4 g sodium acetate (3 eq., 0.065 moles), and 200 ml glacial acetic acid and heated at 115° C. for 16 hours. Thin layer chromatography showed an intense product spot and a light intensity spot corresponding to the starting material. The reaction was quenched by pouring the reaction solution into 300 ml of water and worked up with the addition of 900 ml more water and 500 ml ethyl acetate. The organic phase was separated, washed with 250 ml water, made basic to pH8 with neat sodium bicarbonate, washed with two 250 ml water portions, dried over anhydrous magnesium sulfate, The solvent wasm removed under reduced pressure on the rotary evaporator at 40° C. to give 7.4 g of a crude product as a tan tacky glassy solid.

1.3 g of crude product was purified by flash chromatography, 9:1 ethyl acetate/methanol eluant, to give 1.07 g of methyl α-[2-(3-(3(2H)-pyridazin-3'-on-6'-yloxy) phenyl) oxymethylphenyl]-β-methoxyacrylate as a tan solid product (m.p.=59°–63° C., 67.8% yield extrapolated).

EXAMPLE 6

Methyl α-[2-(3-(2'-Benzylpyridazin-3'-on-6'-yloxy) phenyl)oxymethylphenyl]-β-methoxy Acrylate.
(Table 4; Compound 248)

A 250 ml 3-neck round bottom flask under nitrogen pressure was charged with 0.117 g sodium hydride (1.2 eq., 2.93 mmole, 60% dispersion in mineral oil), washed with hexanes, and 5 ml of DMF. To the base was added, via a pipet, 1.0 g of methyl α-[2-(3-(3(2H)-pyridazin-3'-on-6'-yloxy)phenyl)oxymethylphenyl]-β-methoxyacrylate (1.0 eq., 2.44 mmole) in 8 ml DMF. The reaction mixture was stirred for minutes and 0.42 g benzyl bromide (1.0 eq., 2.44 mmole) in 3 ml DMF was added via a pipet. Thin layer chromatography after 2 hours showed a major product spot and no starting reagent spot. The reaction was quenched at 2.5 hours with the addition of 75 ml of water and 75 ml ethyl acetate. An additional 125 ml of water and ethyl acetate was added to the reaction product. The organic phase was separately washed with three 200 ml water portions, dried over anhydrous magnesium sulfate, the solvent was removed under reduced pressure on the rotary evaporator at 40° C. to give 1.4 g of crude orange/brown product.

The crude product was purified by flash chromatography, 9:1 ethyl acetate/hexanes eluant, to give 0.92 g of methyl α-[2-(3-(2'-benzylpyridazin-3'-on-6'-yloxy) phenyl)oxymethylphenyl]-β-methoxyacrylate as a yellow oil (75.7% yield).

EXAMPLE 7

Preparation of 3-(3-Chloropyridazin-6-yloxy) phenol. (Used to Prepare the Compounds of the Examples 8 and 9)

A one liter, 3-neck round bottom flask under nitrogen pressure was charged with 10.0 g sodium hydride (1.1 eq., 0.25 moles, 60% dispersion in mineral oil), washed with 30 ml hexanes, and then 100 ml DMF was added. With an addition funnel, 25.0 g resorcinol in 100 ml DMF was added to the base while maintaining the temperature <30° C. by using an ice-bath. The reaction mixture was then stirred at ambient temperature for 45 minutes. 3,6-dichloropyridazine (33.9 g, 1.0 eq., 0.23 moles) in 50 ml DMF was added, fairly rapidly, from an addition funnel resulting in an exotherm to 31° C. The reaction mixture was stirred for 26 hours at ambient temperature during which an additional 6.0 grams sodium hydride (0.65 eq., 0.15 moles) in 3 g portions was added. Gas chromatography analysis showed two major products, the monoalkylated/dialkylated in 1.5:1 ratio. The reaction was quenched at 26 hours with the addition of 150 ml ethyl acetate and 150 ml water.

Upon sitting at room temperature, a precipitate of the dialkylated product formed and was filtered to give 8.9 g of tan solids. To improve partitioning, additional water was added to the quenched reaction product for a total of 800 ml (pH9) and extracted with two 300 ml portions of ethyl acetate and then combined. Extracted the 600 ml combined ethyl acetate with two 250 ml basic aqueous portions (25 g of 50% sodium hydroxide) and then combined. The product was precipitated overnight in the basic aqueous solution and was filtered off, washed with water, and dried to give 11.8 g of tan solids. A second basic extraction of the 600 ml product combined ethyl acetate solution (after reducing the volume) followed by acidification and extraction with ethyl acetate gave 0.53 g product after washing with water and ether. The product was precipitated overnight in the first aqueous wash 800 ml (pH9). The precipitate was filtered off and washed with two 100 ml portions of water and 50 ml ether to give 7.9 g of a brown solid. 2.38 g of additional product as a brown solid was obtained from the 800 ml aqueous wash (pH9) by rendering it neutral (pH6), extracting with ethyl acetate, removing the solvent, and washing the solid with two 50 ml portions of water and 50 ml ether. A total of 22.61 g (44.1% yield) of monoalkylated product, 3-(3-chloropyridazin-6-yloxy)phenol, was isolated as a white solid, mp 185°–187° C.

NMR (200 MHz, CDCl3): 6.6–7.9(m,6H), and 8.7(s, 1H).

EXAMPLE 8

Methyl α-[2-(3-(3'-Chloropyridazin-6'-yloxy) phenyl)oxymethylphenyl]-β-methoxyacrylate. (Used to Prepare the Compound of Example 5)

A 250 ml 3-neck round bottom flask, stirring under nitrogen pressure, was charged 0.148 g sodium hydride (1.1 eq., 3.7 mmole, 60% dispersion in mineral oil), washed with hexanes, and 5 ml DMF. With a pipet 0.75 g of 3-(3-chloropyridazin-6-yloxy)phenol (1.0 eq., 3.4 mmole) in 8 ml DMF was added to the base causing an exotherm from 23° C. to 26° C. After stirring 30 minutes, 0.96 g methyl α-(2-bromomethyl phenyl)-β-methoxyacrylate (1.0 eq., 3.4 mmole) in 10 ml DMF was added with a pipet causing a slight exotherm of 2 degrees. Gas chromatography showed 90% product yield after 2.5 hours and after stirring an additional 1 hour the reaction was quenched by the addition of 50 ml water and 50 ml ethyl acetate. The reaction was increased with the addition of 150 ml more of ethyl acetate and water, the organic phase was separated and washed with three 200 ml water portions, dried over anhydrous magnesium sulfate, and the solvent was removed under reduced pressure with a rotary evaporator at 45° C. to give 1.5 g of crude product as a yellow oil.

After purification by flash chromatography, 2:3 ethyl acetate/hexanes eluant, gave 0.82 g (56.6% yield) of methyl α-[2-(3-(3'-chloropyridazin-6'-yloxy)phenyl)oxy methylphenyl]-β-methoxyacrylate as a yellow viscous oil.

NMR (200 MHz, CDCl3): 3.7(s,3H), 3.8(s,3H), 4.95(s, 2H), 6.7–7.6(m,11H).

EXAMPLE 9

Methyl 2-[2-(3-(3'-Chloropyridazin-6'-yloxy)phenyl) oxymethylphenyl]-2-methoxyiminoacetate. (Used to Prepare the Compound of Example 10)

A 500 ml 3-neck round bottom flask, under nitrogen pressure was charged with 2.0 g sodium hydride (1.1 eq., 49.5 mmole, 60% dispersion in mineral oil), washed with hexanes, folowed by 35 ml DMF. To the reaction was added, with a pipet, 10.0 g 3-(3-chloropyridazin-6-yloxy)phenol (1.0 eq., 45.0 mmole) in 35 ml DMF while controlling the exotherm <30° C. with an ice-bath. After stirring 30 minutes, 18.4 g methyl 2-(2-methylphenyl)-2-methoxyiminoacetate (1.0 eq., 45.0 mmole, 70% purity) in 35 ml DMF was added with a pipet causing an exotherm from 24° C. to 31° C. After 1 hour gas chromatography indicated 80% product yield and the reaction was strirred for an additional 1 hour. The reaction was quenched with the addition of 100 ml water and 100 ml ethyl acetate and worked up by the addition of 200 ml more ethyl acetate and 300 ml more water. This solution was acidified with HCl, the organic phase was separated, washed with three 250 ml water portions, dried over anhydrous magnesium sulfate, and the solvent was removed under reduced pressure with a rotary evaporator at 40° C. to give 23.9 g viscous brown oil crude product.

Purification of a combined sample of 3.7 g crude product portion from this reaction and 0.9 g of a similar product by flash chromatography, 1:1 ethyl acetate/hexanes eluant, gave 2.72 g of methyl 2-[2-(3-(3'-chloropyridazin-6'-yloxy) phenyl)oxymethylphenyl]-2-methoxyiminoacetate as a yellow viscous oil (72.1% yieldextrapolated).

NMR (200 MHz, CDCl3): 3.8(s,3H), 4.0(s,3H), 4.95(s, 2H), 6.7–7.6(m,10H).

EXAMPLE 10

Methyl 2-[2-(3-(3(2H)-pyridazin-3'-on-6'-yloxy) phenyl)oxymethylphenyl]-2-methoxyiminoacetate (Table 4, Compound 262)

A one liter, 3-neck, round bottom flask was charged with 20.0 g of methyl 2-[2-(3-(3'-chloropyridazin-6'-yloxy) phenyl)oxymethylphenyl]-2-methoxyiminoacetate (1.0 eq., 0.047 moles), 11.5 g sodium acetate (3 eq., 0.14 moles), and 250 ml glacial acetic acid. The reaction mixture was heated at 117° C. for 5 hours after which thin layer chromatography analysis showed an intense product spot and a light intensity spot corresponding to the starting material.

The reaction was quenched with the addition of 500 ml water and 250 ml ethyl acetate. The organic phase was separated and extracted from the aqueous phase with two 250 ml ethyl acetate portions while adding 250 ml more water to the aqueous phase each time. Combined the ethyl acetate extractions 750 ml, welshed with 750 ml water, washed with 500 aqueous rendered basic to pH8 with neat sodium bicarbonate, washed with two 400 ml water portions, dried over anhydrous magnesium sulfate, and the solvent was removed under reduced pressure on the rotary evaporator to give 19.3 g of crude product, a brown viscous oil.

6 grams of the crude product was titrated with 20 ml of methanol and the solid obtained was filtered, washed with 10 ml of methanol and dried in a vacuum oven to give 2.6 grams of methyl 2-[2-(3-(3(2H)-pyridazin-3'-on-6'-yloxy)phenyl)oxymethyl phenyl]-2-methoxyiminoacetatea, tan solid mp. 115°–117° C., (41.7% extrapolated yield)

EXAMPLE 11

Methyl 2-[2-(3-(2'-n-Propylpyridazin-3'-on-6'-yloxy)phenyl)oxymethylphenyl]-2-methoxyiminoacetate. Table 4 Compound 266)

A 250 ml 3-neck round bottom flask, under nitrogen pressure, was charged with 0.35 g of sodium hydride (1.2 eq., 8.8 mmole, 60% dispersion in mineral oil), washed with hexanes followed by 15 ml DMF. 3.0 g crude methyl 2-[2-(3-(3(2H)-pyridazin-3'-on-6'-yloxy)phenyl)oxymethylphenyl]-2-methoxyiminoacetate (1.0 eq., 7.3 mmole) was added by product in 15 ml DMF. The mixture was stirred 30 minutes, and then 0.90 g propyl bromide (1.0 eq., 7.3 mmole) in 10 ml DMF was added with a pipet to the reaction mixture. Thin layer chromatography analysis after 5 hours showed a major product spot and no starting reagent spot. The reaction was quenched after 5 hours with the addition of 75 ml of water and 75 ml ethyl acetate.

The reaction was increased with the addition of 125 ml more water and ethyl acetate. The organic phase was separated, washed with three 200 ml water portions, dried over anhydrous magnesium sulfate, and removed the solvent under reduced pressure on the rotary evaporator at 40° C. to give 3.2 g crude product, orange/yellow oil.

The crude product was purified by flash chromatography, ethyl acetate eluant, to give 1.3 g of methyl 2-[2-(3-(2'-n-propylpyridazin-3'-on-6'-yloxy)phenyl) oxymethylphenyl]-2-methoxyiminoacetate as a yellow gummy oil (39.5% yield).

EXAMPLE 12

Proton NMR data (200 MHz) are provided for the compounds provided in Table 4.

| EX # | H-nmr (TMS = 0 ppm) |
|---|---|
| 219 | 1.1(t, 3H); 2.2(m, 2H); 3.6(s, 3H); 3.8(s, 3H); 4.9(m, 2H); 5.0(s, 2H); 6.9(m, 2H); 7.1(t, 1H); 7.2(m, 1H); 7.3.–7.5(m, 4H) 7.6(s, 1H); 7.7(m, 1H); 7.8(d, 1H) |
| 220 | 1.4(t, 3H); 3.6(s, 3H); 3.8(s, 3H); 4.3(q, 2H); 5.0(s, 2H); 6.9(m, 2H); 7.1(t, 1H); 7.2(m, 1H); 7.3.–7.5(m, 4H) 7.6(s, 1H); 7.7(m, 1H); 7.8(d, 1H) |
| 221 | 1.1(t, 3H); 2.2(m, 2H); 3.6(s, 3H); 3.75(s, 3H); 3.8(s, 3H); 4.9(m, 2H); 5.0(s, 2H); 6.5(d, 1H); 6.6(m, 1H); 6.8(d, 1H); 7.2(m, 1H); 7.3(m, 2H); 7.4(m, 1H) 7.6(m, 2H); 7.8(d, 1H) |
| 222 | 1.1(t, 3H); 2.2(m, 2H); 3.6(s, 3H); 3.8(s, 3H); 4.9(m, 2H); 5.0(s, 2H); 6.9–7.5(m, 8H); 7.6(s, 1H); 7.8(d, 1H) |
| 223 | 1.1(t, 3H); 2.2(m, 2H); 3.7(s, 3H); 3.9(s, 3H); 4.9(s, 2H); 5.0(s, 2H); 6.9(m, 1H); 7.0(d, 1H); 7.2(d, 1H); 7.25–7.4(m, 5H); 7.5(m, 1H); 7.6(s, 1H); 7.7(d, 1H) |
| 224 | 3.6(s, 3H); 3.75(s, 3H); 3.8(s, 3H); 4.9(s, 2H); 5.0(s, 2H); 6.9(m, 1H); 7.0(d, 1H); 7.2(m, 1H); 7.3–7.5(m, 5H); 7.55(m, 1H); 7.6(s, 1H); 7.7(d, 1H) |
| 225 | 3.6(s, 3H); 3.7(s, 3H); 3.8(s, 3H); 5.0(s, 2H); 5.4(s, 2H); 6.9(d, 1H); 7.0(m, 1H); 7.15(m, 1H); 7.2–7.65(m, 10H); 7.8(d, 1H) |
| 226 | 3.6(s, 3H); 3.7(s, 3H); 5.0(s, 2H); 5.4(s, 2H); 6.5(s, 1H); 6.6(m, 1H); 6.9(d, 1H); 7.2(m, 1H); 7.3–7.6(m, 8H); 7.8(d, 1H) |
| 227 | 3.7(s, 3H); 3.8(s, 3H); 3.9(s, 3H); 5.0(s, 2H); 6.9(m, 2H); 7.2(m, 1H); 7.25–7.4(m, 5H); 7.5–7.8(m, 3H) |
| 228 | 3.7(s, 3H); 3.8(s, 3H); 5.0(s, 2H); 5.4(s, 2H); 7.0(m, 2H); 7.2(m, 1H); 7.3–7.5(m, 6H); 7.5–7.7(m, 5H) |
| 229 | 1.1(t, 3H); 2.2(m, 2H); 3.7(s, 3H); 3.8(s, 3H); 4.9(s, 2H); 5.0(s, 2H); 6.9(m, 1H); 7.0(m, 3H); 7.2(m, 1H); 7.3(m, 3H); 7.5(m, 1H); 7.6(m, 3H) |
| 230 | 3.7(s, 3H); 3.8(s, 3H); 5.0(s, 2H); 5.4(s, 2H); 7.0(m, 2H); 7.2(m, 1H); 7.3–7.5(m, 6H); 7.5–7.7(m, 5H) |
| 231 | 1.4(t, 3H); 3.7(s, 3H); 3.8(s, 3H); 4.3(q, 2H); 5.0(s, 2H); 7.0(m, 2H); 7.2(m, 1H); 7.3–7.5(m, 5H); 7.6(m, 3H) |
| 232 | 1.0(t, 3H); 1.9(q, 2H); 3.7(s, 3H); 3.8(s, 3H); 4.2(t, 2H); 5.0(s, 2H); 7.0(m, 2H); 7.2(m, 1H); 7.3–7.5(m, 5H); 7.6(m, 3H) |
| 233 | 3.0(t, 2H); 3.7(s, 3H); 3.8(s, 3H); 4.5(t, 2H); 5.0(s, 2H); 7.0(m, 2H); 7.2(m, 1H); 7.3–7.5(m, 5H); 7.6(m, 1H); 7.65(s, 1H); 7.7(d, 1H) |
| 234 | 2.6(q, 2H); 3.7(s, 3H); 3.8(s, 3H); 4.3(t, 2H); 5.0(m, 4H); 5.9(m, 1H); 7.0(m, 2H); 7.2(m, 1H); 7.3–7.5(m, 5H); 7.65(m, 3H) |
| 235 | 3.4(s, 3H); 3.6(s, 3H); 3.8(s, 3H); 3.85(m, 2H); 4.4(t, 2H); 5.0(s, 2H); 7.0(m, 2H); 7.2(m, 1H); 7.3–7.5(m, 5H); 7.6(m, 3H) |
| 236 | 3.6(s, 3H); 3.8(s, 3H); 5.0(s, 2H); 6.9(m, 1H); 7.1(d, 1H); 7.2(m, 1H); 7.3–7.6(m, 11H); 7.7(m, 2H) |
| 237 | 3.6(s, 3H); 3.7(s, 3H); 3.8(s, 3H); 5.0(s, 2H); 6.6–6.8(m, 3H); 6.9–7.4(m, 6H); 7.5(m, 1H); 7.6(s, 1H) |
| 238 | 3.7(s, 3H); 3.8(s, 3H); 4.4(m, 1H); 4.6(m, 1H); 4.8(m, 1H); 4.95(m, 1H); 5.0(s, 2H); 7.0(m, 2H); 7.2(m, 1H); 7.3–7.5(m, 5H); 7.5–7.7(m, 3H) |
| 239 | 3.7(s, 3H); 3.8(s, 3H); 4.0(s, 3H); 5.0(s, 2H); 7.0(m, 2H); 7.2(m, 1H); 7.3–7.5(m, 5H); 7.6(m, 1H); 7.7(d, 1H) |
| 240 | 3.6(s, 3H); 3.8(s, 3H); 5.0(s, 2H); 5.7(s, 2H); 6.9(m, 1H); 7.0(d, 2H); 7.2(m, 1H); 7.3–7.45(m, 4H); 7.5–7.8(m, 7H); 8.0(m, 2H) |
| 241 | 2.9(d, 3H); 3.9(s, 3H); 4.0(s, 3H); 5.0(s, 2H); 6.8(m, 1H); 7.0(m, 2H); 7.2(m, 1H); 7.3–7.5(m, 5H); 7.6(m, 1H); 7.7(d, 1H) |
| 242 | 0.3–0.8(m, 4H); 1.4(m, 1H); 3.7(s, 3H); 3.85(s, 3H); 4.1(d, 2H); 5.0(s, 2H); 7.0(m, 2H); 7.1–7.5(m, 6H); 7.6(m, 3H) |
| 243 | 3.6(s, 3H); 3.7(s, 3H); 5.0(s, 2H); 5.5(s, 2H); 6.9(m, 2H); 7.2(m, 1H); 7.3–7.5(m, 7H); 7.5–7.7(m, 4H); 7.8(m, 3H); 7.9(s1H) |
| 244 | 3.7(s, 3H); 3.85(s, 3H); 4.9(q, 2H); 5.0(s, 2H); 7.0(m, 2H); 7.2(m, 2H); 7.4(m, 4H); |

| EX # | H-nmr (TMS = 0 ppm) |
|---|---|
| | 7.6(m, 1H); 7.7(s, 1H); 7.8(d, 1H) |
| 245 | 3.6(s, 3H); 3.7(s, 3H); 5.0(s, 2H); 7.0(m, 2H); 7.2(m, 2H); 7.3–7.5(m, 6H); 7.5–7.7(m, 4H); 7.8(s, 1H) |
| 246 | 3.6(s, 3H); 3.7(s, 3H); 5.0(s, 2H); 7.0(m, 2H); 7.2(m, 2H); 7.3–7.4(m, 6H); 7.5–7.7(m, 4H); 7.8(d, 1H) |
| 247 | 3.7(s, 3H); 3.8(s, 3H); 3.85(s, 3H); 3.9(s, 3H); 5.1(s, 2H); 6.5(m, 2H); 6.9(m, 4H); 7.3(m, 2H); 7.6(m, 2H) |
| 248 | 3.7(s, 3H); 3.78(s, 3H); 4.95(s, 2H); 5.1(s, 2H); 6.7–7.6(m, 16H) |
| 249 | 3.65(s, 3H); 3.8(s, 3H); 4.6(d, 2H); 4.95(s, 2H); 5.15–5.25(m, 2H); 5.8–6.05(m, 1H); 6.65–7.6(9m, 11H) |
| 250 | 1.0–1.1(t, 3H); 2.1–2.25(m, 2H); 3.65(s, 3H); 3.8(s, 3H); 4.7(s, 2H); 4.95(s, 2H); 6.7–7.6(m, 11H) |
| 251 | 0.85–0.95(t, 3H); 1.65–1.8(m, 2H); 3.65(s, 3H); 3.8(s, 3H); 3.9–4.0(t, 2H); 4.95(s, 2H); 6.6–7.6(m, 11H) |
| 252 | 2.7(s, 3H); 2.8(s, 3H); 4.9(s, 2H); 6.65–7.6(m, 11H); 10.6(s, 1H) |
| 253 | 1.0(t, 3H); 1.4(m, 2H); 1.8(m, 4H); 3.7(s, 3H); 3.8(s, 3H); 4.2(t, 2H); 5.0(s, 2H); 7.0(m, 2H); 7.2(m, 1H); 7.3–7.5(m, 5H); 7.6(m, 3H) |
| 254 | 0.9(t, 3H); 1.4(d, 3H); 1.9(m, 2H); 3.7(s, 3H); 3.8(s, 3H); 5.0(s, 2H); 5.2(q, 1H); 7.0(m, 2H); 7.2(m, 1H); 7.3–7.5(m, 5H); 7.6(m, 3H) |
| 255 | 3.7(s, 3H); 3.8(s, 3H); 5.0(s, 2H); 5.4(s, 2H); 6.8(d, 1H); 7.0(m, 3H); 7.2(m, 1H); 7.3–7.5(m, 5H); 7.6(m, 3H) |
| 256 | 2.6(m, 4H); 2.9(m, 2H); 3.7(m, 7H); 3.9(s, 3H); 4.4(t, 2H); 5.0(s, 2H); 7.0(m, 2H); 7.2–7.5(m, 6H); 7.6(m, 3H) |
| 257 | 2.2(m, 2H); 2.7(t, 2H); 3.7(s, 3H); 3.8(s, 3H); 4.3(t, 2H); 5.0(s, 2H); 7.0(m, 2H); 7.1–7.5(m, 11H); 7.6(m, 3H) |
| 258 | 3.7(s, 3H); 3.8(s, 3H); 5.0(s, 2H); 5.6(s, 2H); 6.9(m, 1H); 7.1(d, 1H); 7.15–7.5(m, 10H); 7.6(m, 1H); 7.65(s, 1H); 7.7(d, 1H) |
| 259 | 3.7(s, 3H); 3.8(s, 3H); 5.0(s, 2H); 5.4(s, 2H); 7.0(m, 2H); 7.2–7.5(m, 10H); 7.6(m, 3H) |
| 260 | 3.7(s, 3H); 3.8(s, 3H); 5.0(s, 2H); 5.4(s, 2H); 7.0(m, 2H); 7.2–7.5(m, 10H); 7.6(m, 3H) |
| 261 | 10–1.4(m, 5H); 1.6–2.0(m, 6H); 3.7(s, 3H); 3.8(s, 3H); 4.1(d, 2H); 5.0(s, 2H); 7.0(m, 2H); 7.2(m, 1H); 7.3–7.5(m, 5H); 7.6(m, 3H) |
| 262 | 3.8(s, 3H), 4.0(s, 3H), 5.0(s, 2H), (s, 2H), 6.7–7.6(m, 10H), 10.7(s, 1H) |
| 263 | 3.8(s, 3H), 4.0(s, 3H), 4.95(s, 2H), 5.1(s, 2H), 6.65–7.6(M,15H) |
| 264 | 1.05–1.15(t, 3H), 2.1–2.25(m, 2H), 3.8(s, 3H), 4.0(s, 3H), 4.7(m, 2H), 4.95(s, 2H), 6.7–7.6(m, 10H) |
| 265 | 3.8(s, 3H), 4.0(s, 3H), 4.55–4.65(m, 2H), 4.95(s, 2H), 5.1–5.2(m, 2H), 5.8–6(m, 1H), 6.65–7.6(m, 10H). |
| 266 | 0.85–0.95(t, 3H), 1.6–1.8(m, 2H), 3.8(s, 3H), 3.9–4.0(t, 2H), 4.0(s, 3H), 4.95(s, 2H), 6.6–7.6(m, 10H) |
| 267 | 3.7(s, 3H); 3.8(s, 3H); 4.6(s, 2H); 5.0(s, 2H); 5.3(s, 2H); 6.9(m, 1H); 7.0(d, 1H); 7.2–7.4(m, 11H); 7.5(m, 1H); 7.6(s, 1H); 7.7(d, 1H) |
| 268 | 2.4(t, 2H); 3.7(s, 3H); 3.8(s, 3H); 4.1(m, 2H); 4.5(t, 2H); 5.0(s, 2H); 6.9(m, 5H); 7.1–7.4(m, 7H); 7.5(m, 1H); 7.6(s, 1H); 7.7(d, 1H) |
| 269 | 1.0(m, 6H); 1.5(m, 4H); 2.0(m, 1H); 3.7(s, 3H); 3.8(s, 3H); 4.2(d, 2H); 5.0(s, 2H); 7.0(m, 2H); 7.2(m, 1H); 7.3–7.5(m, 5H); 7.6(m, 3H) |
| 270 | 3.7(s, 3H); 3.8(s, 3H); 5.0(s, 2H); 6.4(s, 2H); 7.0(m, 2H); 7.2(m, 1H); 7.3–7.4(m, 4H); 7.5(m, 1H); 7.6(s, 1H); 7.9(s, 1H); 8.5(s, 1H) |
| 271 | 3.2(t, 2H); 3.7(s, 3H); 3.8(s, 3H); 4.5(t, 2H); 5.0(s, 2H); 7.0(m, 2H); 7.2–7.5(m, 11H); 7.6(m, 3H) |
| 272 | 3.7(s, 3H); 3.8(s, 3H); 4.1(t, 2H); 4.4(t, 2H); 5.0(s, 2H); 7.0(m, 2H); 7.2(m, 1H); 7.3–7.4(m, 5H); 7.6(m, 3H) |
| 273 | 3.7(s, 3H); 3.8(s, 3H); 4.0(t, 2H); 4.6(t, 2H); 5.0(s, 2H); 7.0(m, 2H); 7.2(m, 1H); 7.3–7.5(m, 5H); 7.7(m, 3H) |
| 274 | 3.7(s, 3H); 3.8(s, 3H); 5.0(m, 3H); 5.9(d, 1H); 7.0(m, 2H); 7.2(m, 1H); 7.3–7.5(m, 5H); 7.6(m, 3H); 7.8(dd, 1H) |
| 275 | 1.0(d, 6H); 1.7(m, 3H); 3.7(s, 3H); 3.8(s, 3H); 4.3(m, 2H); 5.0(s, 2H); 7.0(m, 2H); 7.2(m, 1H); 7.3–7.5(m, 5H); 7.7(m, 3H) |
| 276 | 1.7(d, 3H); 3.7(s, 3H); 3.8(s, 3H); 4.8(m, 2H); 5.0(s, 2H); 5.8(m, 3H); 7.0(m, 2H); 7.2(m, 1H); 7.3–7.5(m, 5H); 7.7(m, 3H) |
| 277 | 1.7(s, 3H); 1.9(s, 3H); 3.7(s, 3H); 3.8(s, 3H); 4.8(d, 2H); 5.0(s, 2H); 5.5(m, 1H); 7.0(m, 2H); 7.2(m, 1H); 7.3–7.5(m, 5H); 7.6(m, 3H) |
| 278 | 3.7(s, 3H), 3.8(m, 3H), 5.0(s, 2H), 6.9–7.6(m, 11H), 10.4(m, 1H) |
| 279 | 3.75(s, 3H), 3.85(s, 3H), 4.5–4.6(d, 2H), 5.0(s, 2H), 5.1–5.2(m, 2H), 5.8–6.0(m, 1H), 6.9–7.65(m, 11H) |
| 280 | 1.0–1.1(t, 3H), 2.0–2.2(m, 2H), 3.7(s, 3H), 3.8(s, 3H), 4.65(s, 2H), 5.0(s, 2H), 6.9–7.65(m, 11H) |
| 281 | 1.1(t, 3H); 2.2(m, 2H); 3.6(s, 3H); 3.7(s, 3H); 4.8(s, 2H); 5.0(s, 2H); 6.8(d, 1H); 7.2(m, 1H); 7.4(m, 2H); 7.5(m, 3H); 7.6(m, 1H); 7.7–7.85(m, 3H); 7.9(d, 1H); 8.15(m, 1H) |
| 282 | 3.6(s, 3H); 3.7(s, 3H); 3.8(d, 6H); 5.0(s, 2H); 5.3(bs, 2H); 6.9(m, 2H); 7.2(m, 2H); 7.25–7.5(m, 7H); 7.6(m, 4H) |

EXAMPLE 13

Numerous compounds of this invention were tested for fungicidal activity in vivo against the diseases described below. The compounds were dissolved in a 2:1:1 mixture of water, acetone and methanol (by volume), sprayed onto the plants, allowed to dry (one to two hours) and then the plants were inoculated with the fungus. Each test utilized control plants which were sprayed with the water, acetone and methanol mixture and inoculated with the fungus. The remainder of the technique of each of the tests is given below and the results for various compounds described herein by the Example number in Table 4 against the various fungi at a dose of 300 grams per hectare. The results are reported as percent disease control, compared to the control wherein) one hundred was rated as total disease control and zero was no disease control. The application of the fungi to the test plants was as follows:

Wheat Leaf Rust (WLR)

*Puccinia recondita* (*f. sp. tritici*) was cultured on 7 day old wheat (cultivar Fielder) over a 14 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per flat of twenty of the 2 inch square pots of 7 day old Fielder wheat. After waiting for at least 15 minutes for the oil to evaporate from the wheat leaves, the plants were placed in a dark mist chamber (18°–20° C. and 100% relative humidity) for 24 hours. The plants were then put in the greenhouse for the latent period and scored after 10 days for disease levels. For protective tests the plants are inoculated one day after spraying the plants with the fungicide compounds.

Cucumber Downy Mildew (CDM)

*Pseudoperonospora cubensis* was maintained on leaves of live Bush Champion cucumber plants in a constant temperature room of 18° to 22° C. in humid air with moderate light intensity for 7 to 8 days. A water suspension of the spores from infested leaves was obtained and the spore concentration was adjusted to about $1\times10^5$ per ml of water. Bush Champion cucumber seedlings were inoculated by spraying the underside of leaves with a DeVilbiss atomizer until small drops were observed on the leaves. The innoculated plants were incubated in a mist chamber for 24 hours at about 70° F. and subsequently incubated for 6 to 7 days in a controlled temperature room under mist at 65° to 75° F. Seven days after inoculation the percent disease control was determined.

Grape Downy Mildew (GDM)

*Plasmopara vticola* was maintained on leaves of live grape plants, cv. Delaware, in the controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. Disease control values were recorded as percent control seven days after inoculation.

When tested against cucumber downy mildew at a dose of 300 grams per hectare, Examples 233–242 exhibited 85% or better control. At 300 grams per hectare Examples 227–236 and 238–251 exhibited 75% or better control against wheat leaf rust. Also at 300 grams/hectare, Examples 242–261, 264–269 and 271–277 provided 75% or better control against grape downy mildew.

The dihydropyridazinones and pyridazinones and the enantiomorphs, acid addition salts and metal salt complexes thereof are useful as agricultural fungicides and, as such, can be applied to various loci such as the seed, the soil or the foliage.

The dihydropyridazinones and pyridazinones, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the dihydropyridazinones and pyridazinones, and the enantiomorphs, salts and complexes thereof, display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The dihydropyridazinones and pyridazinones, and the enantiomorphs, acid addition salts and metal salt complexes thereof can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

EXAMPLE 14

Numerous compounds of this invention were tested for insecticidal activity in vivo against the insects described below. The following test method was used to evaluate compounds of the present invention for insectidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

| AW | southern armyworm | *Spodoptera eridamia* |
|---|---|---|
| BB | Mexican bean beetle | *Epilachna varivestis* |
| MTA | two-spotted spider mite | *Teranychus uricate* |

Observations as percent control were made by visual inspection 24–48 hours after spraying.

When tested against southern army worm at 600 grams/hectare Examples 234, 242–245, 253, 255, 258–260, 269–270 and 273–277 provided 90% or better control. When tested against Mexican bean beetle and two-spotted spider mite at 300 grams/hectare Examples 230, 232, 234, 243, 244, 253, 255–257, 268, 269 and 275–277 provided 90% or better control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage. Compositions and formulations according to the present invention may also include known pesticidal compounds. This expands the spectrum of activity of the preparation and may give rise to synergism. Suitable insecticides known in the art inlcude those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredients effectiveness and which by itself has no significant detrimental effect on the soil, equipment, desirable plants, or agronomic enviornment. If desired, adjuvants such as surfactants, stabilizers, antifoam agents and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instantinvention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-Sil®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the pyridazinone, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A dihydropyridazinone and pyridazinone compound having the structure

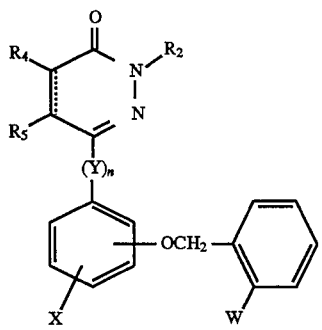

wherein
W is $CH_3-O-A=C-CO(V)CH_3$; A is N or CH; V is O or NH;
wherein
Y is O, S, $NR_1$, or $R_6$, the ring bond containing $R_4$ and $R_5$ is a single or double bond; n is 0 or 1;

X is independently selected from hydrogen, halo, $(C_1-C_4)$ alkyl, $(C_1-C_4)$ alkoxy
and —HC=CH—CH=CH— thereby forming a napthyl ring;

$R_2$ is independently selected from hydrogen, $(C_1-C_{12})$ alkyl, $(C_1-C_{12})$alkoxy, halo$(C_1-C_{12})$alkyl, halo $(C_1-C_{12})$alkoxy, hydroxy$(C_1-C_{12})$alkyl, $(C_1-C_{12})$ alkoxy$(C_1-C_{12})$alkyl, $(C_1-C_{12})$alkoxycarbonyl $(C_1-C_{12})$alkyl, $(C_2-C_8)$alkenyl, halo$(C_2-C_8)$alkenyl, $(C_3-C_{10})$alkynyl, halo$(C_3-C_{10})$alkynyl, $(C_3-C_7)$ cycloalkyl, $(C_3-C_7)$cycloalkyl$(C_1-C_4)$alkyl, epoxy $(C_1-C_{12})$alkyl, $PO(OR_1)_2(C_1-C_{12})$alkyl, $R_1S(O)_2$ $(C_1-C_{12})$alkyl, $(R_1)_3Si(C_1-C_{12})$alkyl, aryl, aryloxy $(C_1-C_{12})$alkyl, arylcarbonyl$(C_1-C_{12})$alkyl, aralkyl, arylalkenyl, heterocyclic, heterocyclic $(C_1-C_{12})$alkyl, N-morpholino$(C_1-C_{12})$alkyl, N-piperidinyl$(C_1-C_{12})$ alkyl;

$R_1$ is independently selected from $(C_1-C_{12})$alkyl, $(C_2-C_8)$ alkenyl and aryl;

$R_4$, and $R_5$ are independently selected from hydrogen, halo, $(C_1-C_8)$alkyl, $(C_1-C_8)$alkoxy, cyano, halo $(C_1-C_{12})$alkyl, $(C_2-C_8)$alkenyl, $(C_3-C_{10})$alkynyl, aryl and aralkyl; and $R_6$ is $(C_1-C_{12})$ alkylenyl and $(C_2-C_{12})$ alkenylenyl;

wherein the foregoing aryl moieties are phenyl or naphthyl, unsubstituted or further substituted with up to three substituents selected from the group consisting of halogen, cyano, nitro, trihalomethyl, phenyl, phenoxy $(C_1-C_4)$alkyl, $(C_1-C_4)$alkylthio, $(C_1-C_4)$ alkylsulfoxide, $(C_1-C_6)$alkoxy and halo$(C_1-C_4)$alkyl;

aralkyl is defined as aryl $(C_1-C_{10})$alkyl wherein aryl is defined above;

heterocyclic moieties are defined as unsubstituted 2-,3- or 4-pyridinyl, pyrazinyl, 2-,4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl or substituted with up to two substituents independently selected from $(C_1-C_2)$alkyl, halogen, cyano, nitro and trichloromethyl.

2. The compound of claim 1 wherein the ring bond between the carbon bonded to $R_4$ and $R_5$ is a double bond.

3. The compound of claim 2 wherein A is CH.

4. The compound of claim 2 wherein A is N.

5. The compound of claim 3 wherein V is O.

6. The compound of claim 4 wherein V is O.

7. The compounds of claim 5 wherein $R_4$ and $R_5$ are hydrogen, the moiety

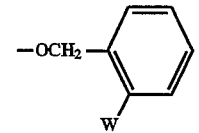

is meta to Y, and $R_2$ is selected from the group consisting of $(C_1-C_{12})$alkyl, $(C_2-C_8)$alkenyl, halo$(C_1-C_{12})$alkyl, aralkyl and halo$(C_2-C_8)$alkenyl.

8. The compound of claim 7 wherein n=0, X is hydrogen and $R_2$ is selected from the group consisting of ethyl, propyl, butyl, vinyl, allyl, chloroethyl, fluoroethyl and aralkyl.

9. The compound of claim 8 wherein aralkyl is selected from halosubstituted benzyl, $(C_1-C_4)$alkyl substituted benzyl, trihalosubstituted benzyl and cyano substituted benzyl.

10. The compound of claim 9 wherein aralkyl is selected from 2-chlorobenzyl, 3-chlorobenzyl, 4-chlorobenzyl, 2-fluorobenzyl, 3-fluorobenzyl, 4-fluorobenzyl, 2-cyanobenzyl, 3-cyanobenzyl, 4-cyanobenzyl and 4-trifluoromethylbenzyl.

11. The compounds of claim 6 wherein $R_4$ and $R_5$ are hydrogen, the moiety

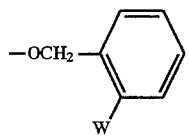

is meta to Y, and $R_2$ is selected from the group consisting of $(C_1-C_{12})$alkyl, $(C_2-C_8)$alkenyl, halo$(C_1-C_{12})$alkyl, halo$(C_2-C_8)$alkenyl and aralkyl.

12. The compound of claim 11 wherein n=0, X is hydrogen and $R_2$ is selected from the group consisting of ethyl, propyl, butyl, vinyl, allyl, chloroethyl, fluoroethyl and aralkyl.

13. The compound of claim 12 wherein aralkyl is selected from halosubstituted benzyl, $(C_1-C_4)$alkyl substituted benzyl and trihalosubstituted benzyl and cyano.

14. The compound of claim 13 wherein aralkyl is selected from 2-chlorobenzyl, 3-chlorobenzyl, 4-chlorobenzyl, 2-fluorobenzyl, 3-fluorobenzyl, 4-fluorobenzyl, 2-cyanobenzyl, 3-cyanobenzyl, 4-cyanobenzyl and 4-trifluoromethylbenzyl.

15. A fungicidal composition for controlling phytophathogenic fungi which comprises an agronomically acceptable carrier and the compound of claim 1 wherein the ratio of the carrier to the compound is 99:1 to 1:4.

16. The composition of claim 15 wherein the ratio of the agriculturally acceptable carrier to compound is 10:1 to 1:3.

17. A method for controlling phytophathogenic fungi which comprises applying to the locus where control is desired the compound of claim 1 at a rate of from 0.005 to 50 kilograms per hectare.

18. The method of claim 17 wherein the compound of claim 1 is applied at the rate of from 0.025 to 10 kilograms per hectare.

19. A method for controlling insects which comprises applying to the insect's habitat the compound of claim 1 at a rate of 0.005 to 10 kilograms per hectare.

20. The method of claim 19 wherein the compound is applied at a rate of 0.01 to 1 kilogram per hectare.

* * * * *

UNITED STATES PATENT AND TRADEMARK OFFICE
CERTIFICATE OF CORRECTION

PATENT NO. : 5,635,494
DATED : June 3, 1997
INVENTOR(S) : Ronald Ross et al.

It is certified that error appears in the above-identified patent and that said Letters Patent is hereby corrected as shown below:

Col. 1, line 10
  replace "Patent"
  with --European Patent--.
Col. 1, line 10
  replace "Sept. 13, 1991"
  with --April 1, 1992--.
Col. 12, line 20
  replace "EP 308404"
  with --European Patent Application Serial No. 91308404.2--.

Signed and Sealed this

Eighth Day of June, 1999

Attest:

Q. TODD DICKINSON

*Attesting Officer*          *Acting Commissioner of Patents and Trademarks*